United States Patent [19]
Farley et al.

[11] Patent Number: 6,033,363
[45] Date of Patent: Mar. 7, 2000

[54] INSULATING SLEEVE FOR A TABLE MOUNTED RETRACTOR

[75] Inventors: Daniel K. Farley, Traverse City; Anthony J. Mulac, East Jordan, both of Mich.

[73] Assignee: Thompson Surgical Instruments, Traverse City, Mich.

[21] Appl. No.: 09/237,746

[22] Filed: Jan. 26, 1999

[51] Int. Cl.⁷ .................................................. A61B 17/00
[52] U.S. Cl. ........................................................ 600/234
[58] Field of Search ................................. 600/201, 203, 600/226, 227, 228, 229, 230, 231, 232, 233, 234; 248/316.1; 128/908

[56] References Cited

U.S. PATENT DOCUMENTS

| | | |
|---|---|---|
| 2,893,378 | 7/1959 | Cooper ..................................... 128/303 |
| 3,221,743 | 12/1965 | Thompson et al. ..................... 128/303 |
| 3,965,890 | 6/1976 | Gauthier . |
| 4,421,108 | 12/1983 | Cabrera et al. . |
| 4,596,484 | 6/1986 | Nakatani ................................. 403/104 |
| 4,617,916 | 10/1986 | LeVahn et al. . |
| 4,813,401 | 3/1989 | Grieshaber . |
| 4,971,038 | 11/1990 | Farley . |
| 5,020,195 | 6/1991 | LeVahn ..................................... 24/514 |
| 5,025,780 | 6/1991 | Farley . |
| 5,224,680 | 7/1993 | Greenstein et al. ................ 600/230 X |
| 5,609,565 | 3/1997 | Nakamura ........................... 600/227 X |
| 5,846,192 | 12/1998 | Teixido ............................... 600/201 X |

*Primary Examiner*—Jeffrey A. Smith
*Attorney, Agent, or Firm*—McAndrews, Held & Malloy, Ltd.

[57] ABSTRACT

A surgical retractor system is provided with an insulating capacity between the retractor blades and surgical table. In particular, the surgical retractor system may include may include a joint clamp with an insulating sleeve within the opening of one of the clamping members. Alternatively, other components of the surgical retractor system may provide the insulating characteristic.

18 Claims, 3 Drawing Sheets

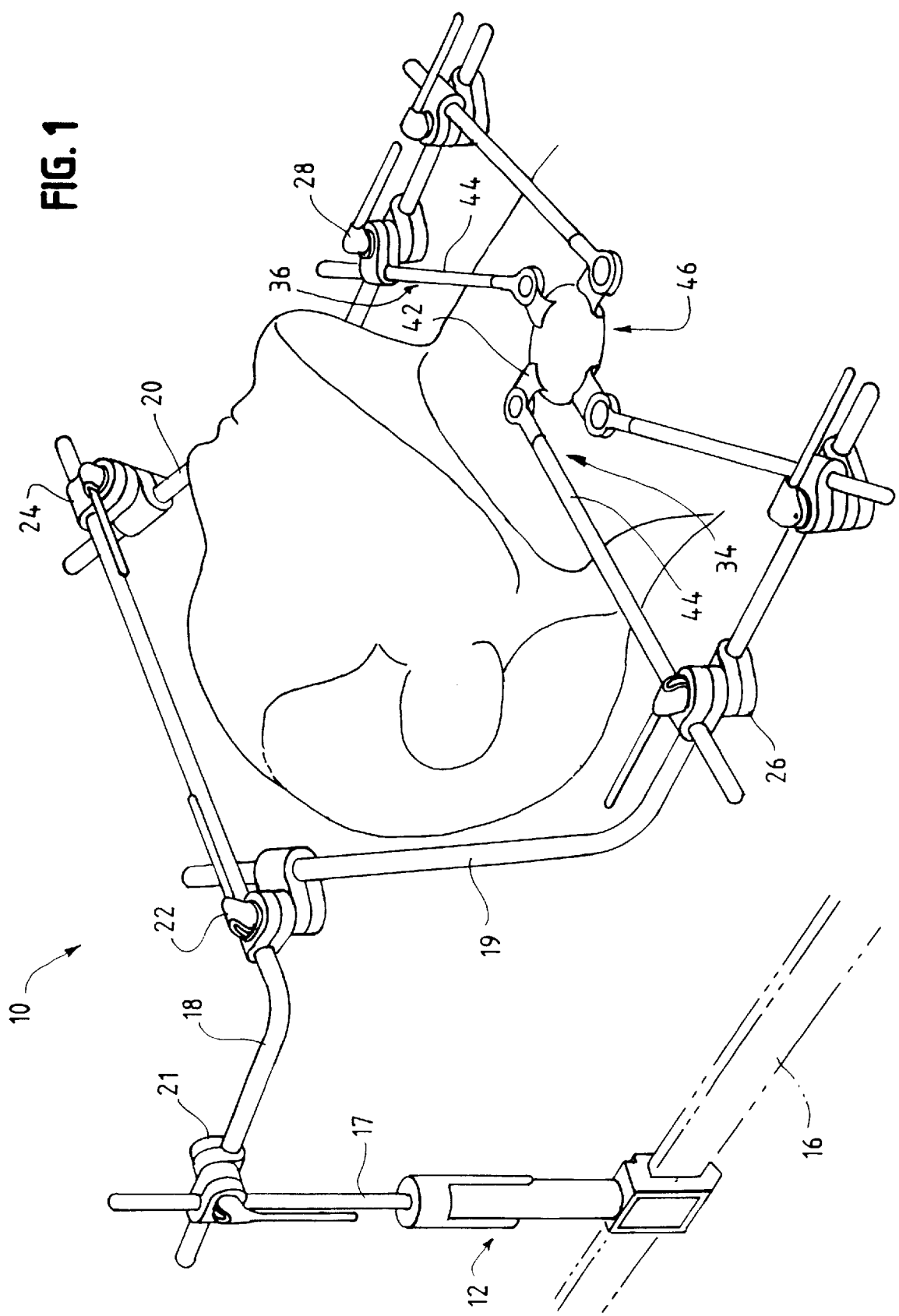

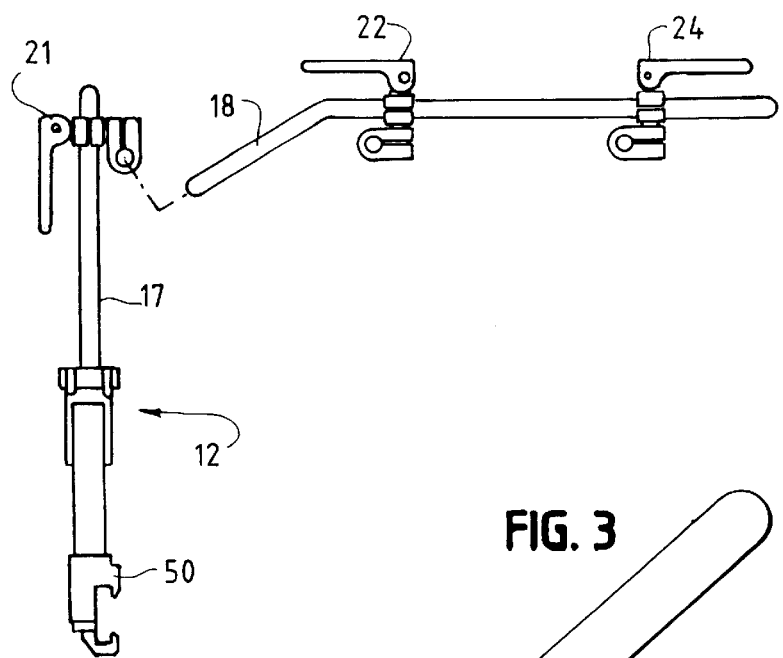
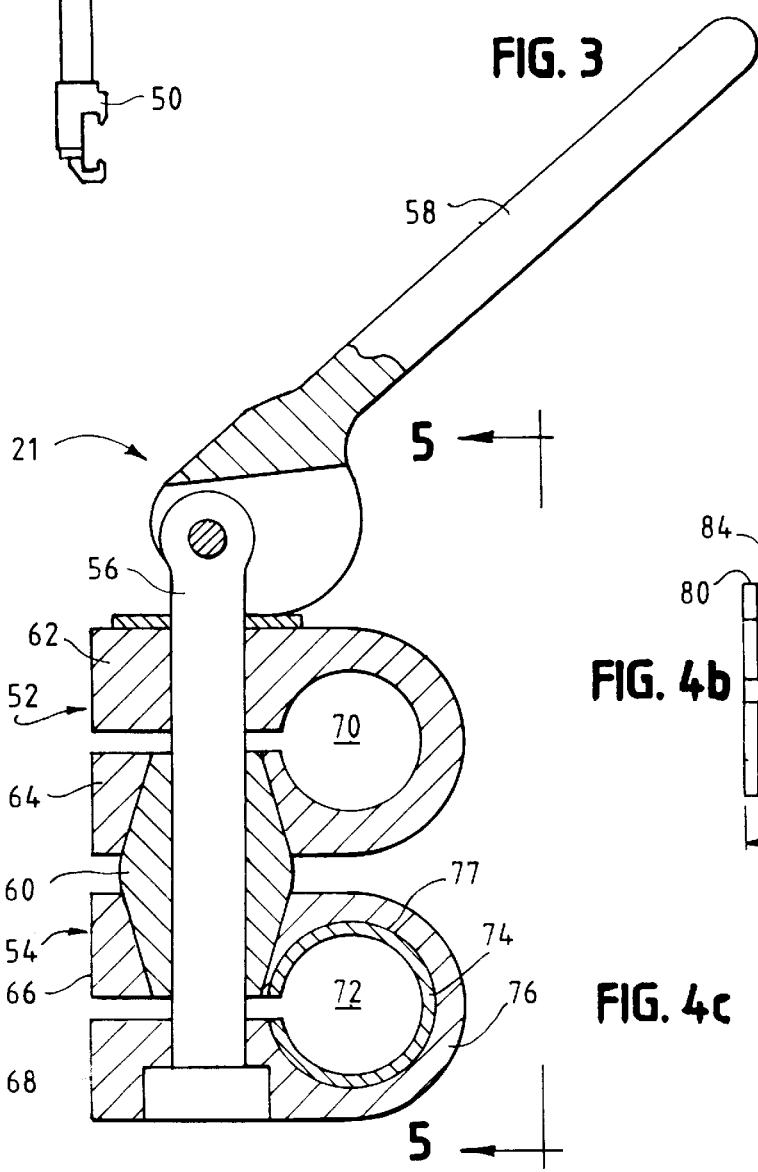
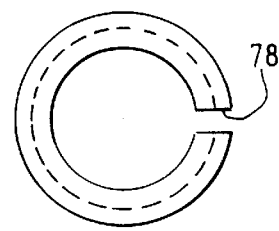
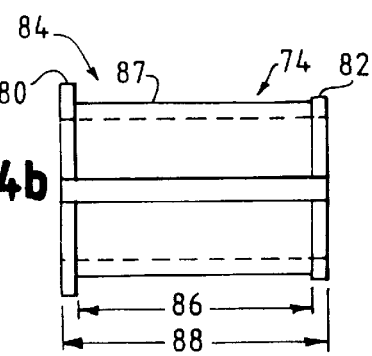
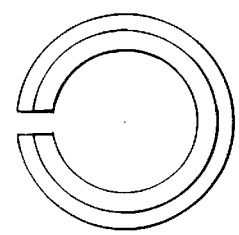

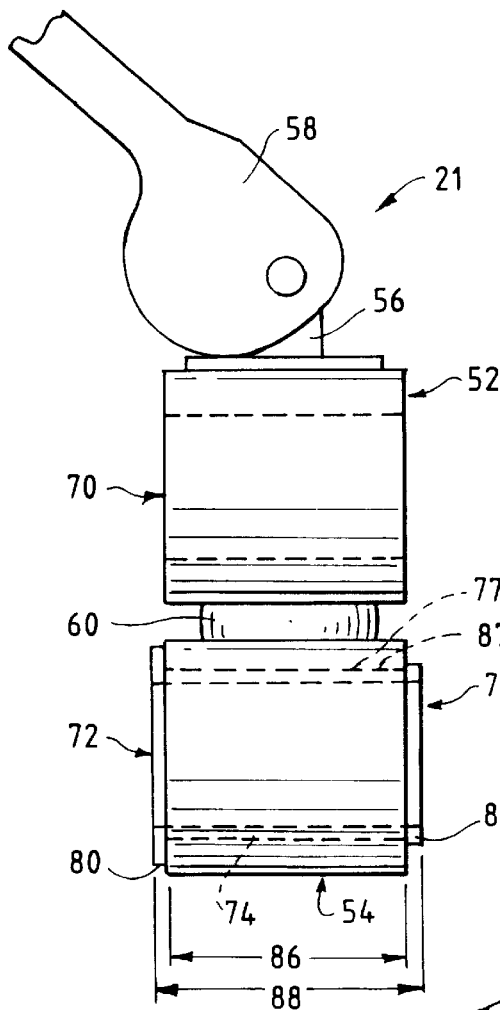
FIG. 5
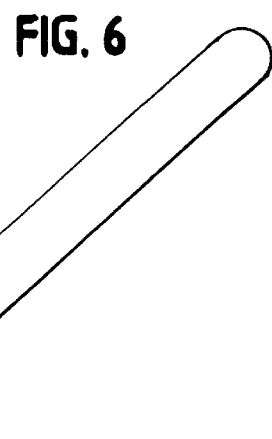
FIG. 6
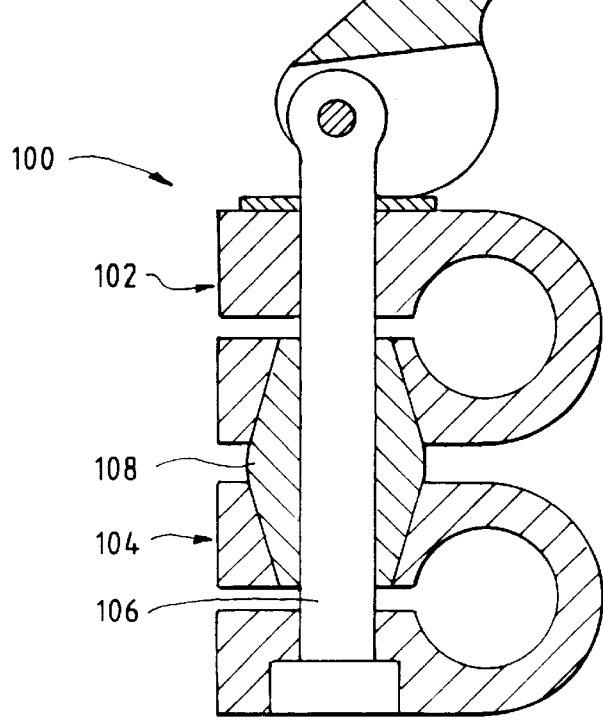

INSULATING SLEEVE FOR A TABLE MOUNTED RETRACTOR

BACKGROUND OF THE INVENTION

The present invention relates to retractor systems for use during invasive surgical medical procedures.

During surgical medical procedures, a surgeon will typically make an incision in a patient to access the site of interest for the particular surgical procedure. To maintain clear access to the site of interest, a surgical retractor system is typically utilized. A surgical retractor system typically consists of a rail clamp, a frame connected to the rail claim by a universal connecting joint mechanism, and retractor blades that are connected to the frame by additional universal connecting joint mechanisms. The rail clamp is commonly secured to an operating table and provides a fixed and sturdy support for the frame and the retractor blades. Each of the components in a typical surgical retractor system is conventionally made of stainless steel. The reason that stainless steel is generally used is that stainless steel is easily sterilized. As would be expected, before any use of the surgical retractor system can be made during a surgical procedure, the system must be thoroughly sterilized for the protection of the patient.

Surgical retractor systems have been made of other materials in the past, such as aluminum and titanium. The common characteristic of all of these materials is that they are highly durable and easily sterilized. That is, these materials are not porous and easily lend themselves to typical sterilization procedures used in modem day hospitals.

One major drawback of the otherwise excellent materials used in the present surgical retractor systems is that they are capable of conducting an electrical current throughout the entire retractor blade's frame and rail clamp down to the surgical table. This can lead to complications in such modem day practices as electro-cauterization where electricity is used to cauterize or stop the bleeding of blood vessels. The electro-cautery units used for such cauterization are similar to arc welders in that the patient is grounded with a negative wire (attached to the patient with conductive and adhesive pads), and the positive wire or pencil is touched to a blood vessel thereby creating a circuit and heat and thereby cauterizing-the blood vessel.

As can be recognized, surgical retractor systems made of the materials identified above and widely used in the industry can interfere with the cauterization of the electro-cautery units. In particular, should the electrical circuit sought to be completed through the patient instead be completed through the surgical retractor system, the desired cauterization will not take place.

Accordingly, it is an object of the invention to provide a surgical retractor system that can be used confidently in surgical procedures where electro-cauterization must be performed.

It is a further object of the invention to provide a surgical retractor system that includes an electrical insulation between the surgical retractor blades and the surgical table on which the rail clamp is mounted.

A further object of the invention is to provide a surgical retractor system that includes electrical insulation and maintains the effective sterilization characteristics of present surgical retractor systems.

SUMMARY OF THE INVENTION

These and other objects of the invention are achieved in a surgical retractor system which includes at least one universal connecting joint mechanism that includes at least one clamping member fitted with a non-conductive sleeve. The sleeve may be designed to fit within a conventional universal clamping mechanism. Alternatively and preferably, a universal clamping mechanism can be designed such that the universal clamping mechanism in combination with the non-conductive sleeve can be used on conventional surgical retractor systems already in the field. Preferably, the universal clamping mechanism that is fitted with the non-conductive sleeve is that mechanism that attaches the frame to the rail clamp. In this way, only one such fitted universal clamping mechanism is required to completely insulate the frame of a surgical retractor system from the surgical table. Alternatively, the universal clamping mechanisms that connect the retractor blades to the frame may be fitted with the sleeve. A further alternative is where the appropriate universal clamping mechanism in part or in its entirety is made of a non-conductive material.

A BRIEF DESCRIPTION OF THE DRAWINGS

FIG. 1 is a perspective view of a typical surgical retractor system.

FIG. 2 is an elevated view of a rail clamp with a universal clamping mechanism of the present invention and a cross bar for insertion into the insulated universal clamping mechanism.

FIG. 3 is a partial cross-sectional view of the universal clamping mechanism of the present invention with an insulating sleeve.

FIG. 4 is an elevated view of the non-conductive sleeve of the present invention.

FIG. 5 is an elevated view of the insulating universal clamping mechanism of the present invention.

FIG. 6 is an elevated view of an alternative insulating universal clamping mechanism of the present invention.

DETAILED DESCRIPTION OF A PREFERRED EMBODIMENT

In the following detailed description, spatially orienting terms are used such as "left," "right," "vertical," "horizontal," and the like. It is to be understood that these terms are used for convenience of description of the preferred embodiments by reference to the drawings. These terms do not necessarily describe the absolute location in space, such as left, right, upward, downward, etc., that any part must assume.

As shown in FIG. 1, a surgical retraction system 10 includes an adjustable rail clamp 12 which is securable to a conventional surgical table 16. A second adjustable rail clamp (not shown) may be secured to the opposite side of the surgical table for increased stability if desired or needed. A post 17 extends vertically from clamp 12 to provide support for a cross bar 18 which in turn provides support for a pair of extension arms 19, 20. Cross bar 18 is secured to post 17 by a multi-directional joint clamp 21. Extension arms 19, 20 are respectively secured to cross bar 18 by a pair of multi-directional joint clamps 22, 24. Additional joint clamps 26, 28 are disposed along extension arms 19, 20 for rigidly securing any number of retractor blades 34, 36 to extension arms 19, 20. As will suggest itself, extension arm 19 may be secured directly to post 17 by a joint clamp, thus in many circumstances eliminating the need for cross bar 18.

The purpose of this frame is to securely connect the retractor blades 34, 36 to the rail clamp 12 to eliminate unwanted relative movement between the retractor blades 34, 36 and the surgical table 16, this may be accomplished by connecting the retractor blades to the cross bar 18 directly or through extension arms 19, 20, or, as already noted, by connecting extension arms 19, 20 directly to the rail clamp.

Each retractor blade 34, 36 includes a blade portion 42 and a retractor arm 44. Blade portion 42 extends downwardly into the incision 46 made by the surgeon. Blade portion 42 is used to retract anatomy to make the incision 46 accessible to the surgeon.

FIG. 2 is an elevated view of the rail clamp 12 and cross bar 18. Of course, as noted above, extension arm 19 or 20 may be connected directly to adjustable rail clamp 12. The rail clamp includes a clamp 50 that may be secured to surgical table 16 (FIG. 1). This may be a conventional clamp as presently used in the industry and provides for a secure attachment of the adjustable rail clamp 12 to the surgical table 16. Multi-directional joint clamp 21 is shown at the upper most extremity of post 17. This position of the multi-directional joint clamp 21 enables the user to locate cross bar 18 at a height sufficient for the surgical retractor system 10 (FIG. 1) to be used during surgical procedures. FIG. 2 further shows joint clamps 22, 24 in their position on cross bar 18. Clamps 22 and 24 may be identical to each other or different depending on the intended use of each of those clamps. Additionally, these joint clamps 22, 24 may each be the same as or different to the multi-directional joint clamp 21 on post 17.

FIG. 3 shows an elevated partial cross-sectional view of multi-directional joint clamp 21. Joint clamp 21 includes a first clamping member 52 and a second clamping member 54. Such a joint clamp 21 generally includes a central shaft 56 as well as a mechanism for bringing the first clamping member 52 and second clamping member 54 into its clamping and unclamping positions. That mechanism may be a cam lever 58. The joint clamp 21 may also include a washer 57 positioned between the cam lever 58 and the first clamping member 52. The joint clamp 21 may further include a wedge member 60 to insure adequate constriction of the resilient legs 62, 64 of first clamping member 52 and resilient legs 66, 68 of second clamping member 54.

The first clamping member 54 includes a passage 70 which is intended to accommodate post 17 of rail clamp 12 (FIG. 2). Similarly, second clamping member 54 includes a passage 72. Passage 72 is intended to accommodate cross bar 18 (FIG. 2). This type of joint clamp is more fully described in co-pending patent application Ser. No. 08/482, 023, now U.S. Pat. No. 5,897,087, and that description is incorporated here by reference.

As illustrated in FIG. 3, passage 72 of second clamping member 54 has the same diameter as passage 70 of the first clamping member 52. In such a case, cross bar 18 would be required to have the same diameter as post 17 to fit snuggly within passage 72. This is the customary configuration used in present surgical retractor systems. In this preferred embodiment, the non-conductive joint clamp 21 can be used with conventional retractor systems already in use in the industry. That is, new rail clamps 12 with a post 17 of smaller diameter will not be necessary and new cross bars 18 with reduced diameter will also not be necessary.

The component that primarily defines passage 72 is insulating sleeve 74. Insulating sleeve 74 may be a disposable split bushing that can easily slide into the opening 77 defined by the curved portion 76 of the second clamping mechanism 54. The size of a typical passage 70 in existing joint clamps 21 is one-half ($\frac{1}{2}$) inch. In order to appropriately accommodate insulating sleeve 74 in the opening 77 defined by curved portion 76 of the second clamping member 54, such that passage 72 retains a diameter of one-half ($\frac{1}{2}$) inch, the opening 77 of curved portion 76 of second clamping member 54 may have an inside diameter of five-eighths ($\frac{5}{8}$) inch. In order to provide passage 72 with a one-half ($\frac{1}{2}$) inch diameter, the insulating sleeve 74 may have a thickness of one-sixteenth ($\frac{1}{16}$) inch. The added thickness (a total of one-eighth ($\frac{1}{8}$) inch) of the insulating sleeve 74 within the internal opening 77 defined by curved portion 76 of second clamping member 54 will provide passage 72 with a diameter of one-half ($\frac{1}{2}$) inch. In such a system, if the insulating sleeve 74 was not put in place, the second clamping member 54 could not be used with a conventional post 17 or cross bar 18 having the typical one-half ($\frac{1}{2}$) inch diameter. Of course, these dimensions are identified only for purposes of illustration and should not be construed to limit the scope of the present invention in any way.

An alternative arrangement may be to retrofit a standard universal clamping mechanism with an insulating sleeve. In this alternative arrangement, a typical clamping mechanism has clamping members with openings or passages of typically one-half ($\frac{1}{2}$) inch. The insertion of an insulating sleeve into one of these openings would result in a passage on the order of three-eighths ($\frac{3}{8}$) inch. This of course calls for a rail clamp post or cross bar (or both) having a portion with a diameter reduced to correspond to the reduced opening of the retrofitted standard universal clamping mechanism. As above, the dimensions identified in connection with this alternative embodiment are simply for illustrative purposes and are not intended to limit the scope of the invention.

FIG. 4 shows two end views of insulating sleeve 74 and an elevated side view of the insulating sleeve 74. FIG. 4 illustrates that insulating sleeve 74 has a split 78 which enables the insulating sleeve 74 to be resiliently inserted into the opening 77 in the curved portion 76 of the second clamping member 54 (FIG. 3). FIG. 4b shows the large lip 80 and small lip 82 that are positioned at opposite ends of the insulating sleeve 74. Lips 80 and 82 extend radially from the central portion 87 of the outer surface 84 of the insulating sleeve 74. The outer surface 84 of insulating sleeve 74 can be defined by two lengths. The first length 88 is the entire length of the insulating sleeve 74. The second length 86 is shorter than the first length 88 and should correspond to the width of second clamping member 54 such that large lip 80 and small lip 82 act as retaining clips on opposite sides of the second clamping member 54 while the central portion 87 directly abuts the opening 77 of the curved portion 76 of the second clamping member 54 (FIG. 3). In other words, large lip 80 and small lip 82 do not reside within the opening 77 defined by the curved portion 76 of the second clamping member 54. The insulating sleeve 74 can be removed from the opening defined by the curved portion 76 by simply squeezing its ends together as permitted by the split 78 and pushing the insulating sleeve 74 through the opening 77 defined by the curved portion of the second clamping member.

Typically, insulating sleeves 74 as shown in FIG. 4 can be made from thermoplastic resins and in particular from the following polymers: Radel R (available from Amoco), P.E.E.K. (poly-ether-ether-ketone), Ulten (available from General Electric) and polycarbonate. Preferably, the polymer insulating sleeve will be made of Radel or Peek. Radel in particular has been found to be appropriate for sterilization and will likely be usable with the system for a number of separate uses. These polymer insulating sleeves 74, however, naturally degrade with repeated use and are not intended as permanent sleeves for the joint clamp. Instead, the polymer insulating sleeve 74 will likely require replacement after several uses.

FIG. 5 is an elevated view of the insulating joint clamp 21 of the present invention. As can be seen, FIG. 5 is an end view of the joint clamp 21 of FIG. 3 and includes the clamping members 52, 54, shaft 56, cam lever 58, washer 57, and wedge member 60. Passages 70, 72 are shown in phantom as is insulating sleeve 74.

Insulating sleeve is fitted into the opening 77 of the second clamping member 54. The central portion 87 directly abuts the opening 77 while the large lip 80 and the small lip 82 act as retaining clips on opposite sides of the second clamping member 54. That is, the length 86 should be at least as wide as the width of the second clamping member 54.

FIG. 6 is an elevated view of an alternative insulating joint clamp of the present invention. As is evident from the embodiment of the invention described above, one object of the present invention is to insulate the retractors on the frame of a surgical retractor system from the rail clamp and thus the surgical table. More simply, the rod held by one clamping member must be insulated from the rod held in the second clamping member.

Other components of the joint clamp 100 may provide the necessary insulating characteristic to the surgical retractor system. For example, the first clamping member 102 may be made of an insulating material. The insulating material, however, must be such that it can firmly and securely clamp onto a standard rod (not shown) to prevent relative movement between the first clamping member 102 and the rod.

Alternatively, the second clamping member 104 may be made of an insulating material, the shaft 106 and wedge 108 may be made of an insulating material, or the joint clamp 100 in its entirety may be made of an insulating material.

Still a further alternative may be to use conventional joint clamps but to use one or more insulating rods. For example, the rods shown in FIG. 1 may be made to provide the necessary insulating. Post 17, cross bar 18, or extension arms 19, 20 may each be made of insulating material, either in combination or separately to insulate the retractor blades 34, 36 from the surgical table. 16.

While particular embodiments of the invention have been shown, it will be understood that the invention is not limited thereto since modifications may be made by those skilled in the art, particularly in light of the foregoing teaching. It is, therefore, the appended claims which define the true spirit and scope of the invention.

What is claimed is:

1. A surgical retractor system comprising
   a rail clamp, the rail clamp including a clamp for securing the rail clamp to a surgical table and a generally vertically extending post;
   a cross bar, the cross bar extending generally horizontally;
   a joint clamp for securing the cross bar to the post of the rail clamp, the joint clamp including a first clamping member having a first passage adapted to accommodate the generally vertically extending post of the rail clamp and a second clamping member, the second clamping member having an opening including an insulating sleeve defining a second passage adapted to accommodate the generally horizontally extending cross bar; and
   at least one retractor blade connected to the cross bar.

2. The surgical retractor system of claim 1 in which the first passage and the second passage have equal diameters.

3. The surgical retractor system of claim 1 in which the insulating sleeve has an outer surface that includes a middle portion, a first lip and a second lip, the middle portion having a length at least the width of the second clamping member and adapted to abut the opening of the second clamping member and the first and second lips positioned at opposed ends of the insulating sleeve and adapted to retain the middle portion of the insulating sleeve within the opening of the second clamping member.

4. The surgical retractor system of claim 3 in which the insulating sleeve includes a split permitting the resilient compression of the insulating sleeve for insertion into and removal from the opening of the second clamping member.

5. The surgical retractor system of claim 1 in which the first clamping member includes a first opening and an insulating sleeve within the opening defining the first passage.

6. A joint clamp for use in a surgical retractor system comprising
   a first clamping member, the first clamping member having a first passage;
   a second clamping member, the second clamping member having an opening;
   an insulating sleeve adapted to fit within the opening of the second clamping member to define a second passage.

7. The joint clamp of claim 6 in which the first passage and the second passage have equal diameters.

8. The joint clamp of claim 7 in which the insulating sleeve includes a split permitting the resilient compression of the insulating sleeve for insertion into and removal from the opening of the second clamping member.

9. The joint clamp of claim 6 in which the insulating sleeve has an outer surface that includes a middle portion, a first lip and a second lip, the middle portion having a length at least the width of the second clamping member and adapted to abut the opening of the second clamping member and the first and second lips positioned at opposed ends of the insulating sleeve and adapted to retain the middle portion of the insulating sleeve within the opening of the second clamping member.

10. A kit for a surgical retractor system comprising
    a rail clamp, the rail clamp including a clamp for securing the rail clamp to a surgical table and a generally vertically extending post;
    a cross bar;
    a joint clamp for securing the cross bar to the post of the rail clamp, the joint clamp including a first clamping member having a first passage adapted to accommodate the post of the rail clamp and a second clamping member, the second clamping member having an opening;
    an insulating sleeve adapted for insertion into the opening of the second clamping member to define a second passage adapted to accommodate the cross bar; and
    at least one retractor blade for connection to the cross bar.

11. The kit for a surgical retractor system of claim 10 in which the first passage and the second passage have equal diameters.

12. The kit for a surgical retractor system of claim 10 in which the insulating sleeve has an outer surface that includes a middle portion, a first lip and a second lip, the middle portion having a length at least the width of the second clamping member and adapted to abut the opening of the second clamping member and the first and second lips positioned at opposed ends of the insulating sleeve and adapted to retain the middle portion of the insulating sleeve within the opening of the second clamping member.

13. The kit for a surgical retractor system of claim 10 in which the insulating sleeve includes a split permitting the resilient compression of the insulating sleeve for insertion into and removal from the opening of the second clamping member.

14. A surgical retractor system comprising a rail clamp;

a retractor blade connected to the rail clamp; and means for electrically insulating the retractor blade from the rail clamp.

15. The surgical retractor system of claim 14 wherein the means for electrically insulating the retractor blade from the rail clamp comprises a joint clamp having a first clamping member and a second clamping member with the first clamping member being electrically insulated from the second clamping member.

16. The surgical retractor system of claim 14 wherein the means for electrically insulating the retractor blade from the rail clamp comprises a post made of an insulating material.

17. The surgical retractor system of claim 14 wherein the means for electrically insulating the retractor blade from the rail clamp comprises a cross bar made of an insulating material.

18. The surgical retractor system of claim 14 wherein the means for electrically insulating the retractor blade from the rail clamp comprises an extension arm made of an insulating material.

* * * * *